(12) United States Patent
Kuri-Harcuch et al.

(10) Patent No.: US 6,713,084 B1
(45) Date of Patent: Mar. 30, 2004

(54) METHODS FOR PROMOTING HEALING OF SKIN RESURFACING WOUNDS

(75) Inventors: Walid Kuri-Harcuch, Brookline, MA (US); Yesid Bolivar-Flores, Delegacion Tlalpan (MX)

(73) Assignee: Celadon Science, LLC, Wellesley, MA (US)

( * ) Notice: Subject to any disclaimer, the term of this patent is extended or adjusted under 35 U.S.C. 154(b) by 0 days.

(21) Appl. No.: 09/341,745

(22) PCT Filed: Jan. 16, 1998

(86) PCT No.: PCT/US98/00978

§ 371 (c)(1),
(2), (4) Date: Oct. 19, 1999

(87) PCT Pub. No.: WO98/31317

PCT Pub. Date: Jul. 23, 1998

Related U.S. Application Data
(60) Provisional application No. 60/037,748, filed on Jan. 17, 1997.

(51) Int. Cl.⁷ .......................... A61F 13/00; A61L 15/00
(52) U.S. Cl. .................. 424/443; 424/444; 424/445; 424/449
(58) Field of Search ................... 424/443, 444, 424/445, 448, 449; 435/240.23

(56) References Cited

U.S. PATENT DOCUMENTS

| | | |
|---|---|---|
| 4,865,871 A | 9/1989 | Livesey et al. |
| 5,145,770 A * | 9/1992 | Tubo et al. ................. 435/1 |
| 5,197,985 A | 3/1993 | Caplan et al. |
| 5,298,417 A * | 3/1994 | Cancedda et al. ........ 435/240.1 |
| 5,405,742 A | 4/1995 | Taylor |
| 5,440,018 A | 8/1995 | Ohmura et al. |
| 5,580,714 A | 12/1996 | Polovina |
| 5,580,781 A * | 12/1996 | Naughton et al. .... 435/240.243 |
| 6,106,514 A * | 8/2000 | O'Donnell, Jr. |

FOREIGN PATENT DOCUMENTS

WO    WO 94/13135 A1    6/1994

OTHER PUBLICATIONS

Reiners et al., "Cryopreservation of Human Granulocyte–Macrophage Progenitor Cells (CFU–c) with Dimethyl Sulfoxide (DMSO) and Human Serum Albumin", Cryo–Letters, (1986), 7:327–337, pub. Cambridge, U.K.

Storey, "Biochemistry of natural freeze tolerance in animals: molecular adaptations and applications to cryopreservation", Biochemistry and Cell Biology, Apr., 1990, vol. 68–No. 4, pp–687–698, pub. Ottawa, Ont.

* cited by examiner

*Primary Examiner*—Thurman K. Page
*Assistant Examiner*—Isis Ghali
(74) *Attorney, Agent, or Firm*—Wolf, Greenfield & Sacks, P.C.

(57) ABSTRACT

The present invention provides methods for promoting healing of wounds which result from skin resurfacing procedures, e.g., from laser surgery to remove or alter superficial features of the skin. The methods involve the application of a sheet of cultured epithelial cells to the laser skin resurfacing would of a subject in need of such treatment. The methods promote faster healing of skin resurfacing wounds relative to prior art methods of healing such wounds.

7 Claims, No Drawings

METHODS FOR PROMOTING HEALING OF SKIN RESURFACING WOUNDS

This application claims the benefit of Provisional application Ser. No. 60/037,748, filed Jan. 17, 1997.

FIELD OF THE INVENTION

The invention involves methods of using sheets of cultured epithelial cells to promote healing of skin resurfacing wounds.

BACKGROUND OF THE INVENTION

Removal of superficial skin features has been accomplished previously by procedures such as dermabrasion and chemical peels using acids or other caustic agents such as phenol. These procedures remove portions of the outer and middle layers of the skin, the epidermis and dermis, to remove wrinkles, discolorations, scars, roughness and other features of damaged skin. More recently, short-pulse or rapid scanning lasers (e.g. $CO_2$ lasers, excimer lasers) have been used for the same purpose. Whereas dermabrasion and chemical peels can result in scarring, discoloration and/or changes in the smoothness of the treated skin relative to surrounding skin, laser treatment typically yields removal of the unwanted skin feature without residual scarring or bleeding.

One of the difficulties which accompanies laser skin resurfacing is the lengthy and often painful post-treatment period. After the laser treatment, ointments and dressings are applied to the wound site to lessen drying of the treated skin and promote healing of the wound. Dressings must be changed often, because the treated skin oozes for 7–14 days following treatment (Arndt and Thomas, Harvard Health Letter, 21:4–5 (1996)). To alleviate the pain associated with the laser resurfacing and to foster healing, patients must perform a series of washes and soaks of the wound site, and then apply additional ointments and dressings to the wound site. Such repetitive treatment of the wound site is painful and inconvenient for the patient, and if not performed properly, increases the risk of infection.

Thus, there exists a need for a procedure which will reduce the need for a patient's self-treatment treatment of the laser wound site. Further, there is a need for a treatment of laser skin resurfacing wound sites that will promote faster healing of the wound, lessen pain and reduce the possibility of infection of the wound site. Additionally, there is a need for a treatment which need not be changed while the skin resurfacing wound heals.

Sheets of cultured epithelial cells can be used as replacements for human skin autografts and allografts. Indications for use of cultured epithelial cell sheets include those for which traditional skin autografts are used, including large surface area burns and chronic skin ulcers. As substitutes for allografts, sheets of cultured epithelial cells also are used for, inter alia, healing of split-thickness autograft donor sites (see, e.g., EP 0 296 475, Cancedda et al.; PCT/AUS91/03582, Tubo et al.)

SUMMARY OF THE INVENTION

The present invention provides methods for promoting healing of wounds which result from skin resurfacing procedures by laser surgery to remove or alter superficial features of the skin. The methods promote faster healing of skin resurfacing wounds relative to prior art methods of healing such wounds. The methods also reduce pain and complications associated with such wounds. The methods involve the application to the skin of sheets of cultured cells.

According to one aspect of the invention, a method for promoting healing of a skin resurfacing wound is provided. The method involves applying a sheet of cultured epithelial cells to the wound of a patient in need of such treatment. Preferably, the sheet substantially covers the wound. The wound is a laser induced wound from a laser skin resurfacing treatment.

In certain embodiments, the sheet of cultured epithelial cells is a preserved sheet. Preferably, the preserved sheet of cultured epithelial cells is dried or frozen. If the preserved sheet of cells is frozen, then it is thawed prior to direct application to the wound. If the preserved sheet of cells exists in a dry state, then it can be applied to the wound after rehydration or applied directly to the wound without prior rehydration, the dried cells rehydrating at the wound site.

In other embodiments, the sheet of cultured epithelial cells is disposed on a backing. The backing provides structural support to the sheet of cells during the step of applying the sheet to the wound. Preferably, the backing is a gauze mesh, but also could be a hydrocolloid, a Teflon sheet, or a collagen matrix. The method optionally provides for covering the applied sheet of cultured epithelial cells with a dressing.

In still other embodiments, the cultured epithelial cells are attached to a substratum or mixed with a gel. Preferably, the substratum is selected from the group consisting of microbeads, hyaluronic acid, collagen, fibrin glue and polymers.

The invention also involves the use of a sheet of cultured epithelial cells in the preparation of a medicament for treating a laser skin resurfacing wound. The sheet of cultured epithelial cells provides, among other things, a covering to prevent dehydration, cell-cell contact between the surface of the sheet of cultured epithelial cells and the skin, and factors released by the sheet of cultured epithelial cells which promote healing.

The invention also involves a cosmetic treatment of skin. In a first step, the skin is treated by lasar surgery to remove or alter superficial features of the skin. In a second step, the lasar skin resurfacing wound created by the lasar treatment then is covered with a sheet of cultured epithelial cells.

These and other aspects of the invention are described in greater detail below.

DETAILED DESCRIPTION OF THE INVENTION

The invention involves methods of promoting healing of a laser skin resurfacing wound. The methods involve the application to the laser skin resurfacing wound of a sheet of cultured epithelial cells. Preparation of such a sheet of cultured epithelial cells is disclosed, for example, in PCT Patent Application PCT/US95/14648. By "applying" is meant placing the sheet of cultured epithelial cells upon the wound and, optionally, covering the sheet of cultured epithelial cells with a dressing. Thus, applying a sheet of cultured epithelial cells is performed according to any standard medical procedure for applying a dressing to a wound. If necessary, after applying it, one can attach the sheet of cultured epithelial cells to the tissue surrounding the laser skin resurfacing wound by means of a dermatologically-acceptable adhesive, for instance a biological adhesive such as fibrin glue.

The wound to be treated is created during the process of skin resurfacing by laser irradiation. Skin can be "resurfaced" by the use of different lasers, such as a short pulse or rapid scanning carbon dioxide laser, or an excimer laser. Other lasers useful for performing skin resurfacing will be known to one of ordinary skill in the art. By "resurfacing" is meant the removal of selected portions of the epidermis and underlying tissue, to achieve a desired removal of unwanted skin features. The laser emits a beam of light which imparts energy to the epidermis in a highly localized fashion. The portion of the skin contacted by the laser beam is vaporized, thus removing unwanted features such as wrinkles, discolorations, and other surface irregularities. The laser skin resurfacing wound does not extend to the deeper, unvaporized layers of the skin remaining at the site of laser treatment. By migration and proliferation of cells originating in hair follicles or sweat glands in deeper layers, a new upper layer of skin lacking the unwanted surface features is generated.

Traditional therapy for promoting healing of the laser skin resurfacing wound includes the application of ointments and nonbiological dressings, which must be changed frequently. The newly generated layer of skin grows and differentiates underneath the dressing to fill in the laser wound.

The application of a sheet of cultured epithelial cells enhances the healing process by providing to the wound growth factors, extracellular matrix components and other wound healing agents. The present invention facilitates the application of a physiologically relevant amount of growth factors, extracellular matrix components and other wound healing agents at the wound site. Additional applications of wound healing agents are not required.

The method of the invention also facilitates application of a physiologically relevant spectrum of wound healing agents. The sheet of cultured epithelial cells, once applied, releases biological factors which promote the migration, proliferation and/or differentiation of the epidermal cells to heal the wound. For example, a sheet of cultured epithelial cells can release known growth factors such as fibroblast growth factors (FGFs), basement membrane components and the like, but also will release growth factors, extracellular matrix components and other wound healing agents which have not been characterized.

Of course, like prior art methods in which a traditional wound dressing is applied to the laser skin resurfacing wound, applying a cultured epithelial cell sheet provides a protective barrier to the laser wound which keeps the wound from dehydrating and which excludes foreign matter including microorganisms such as bacteria and viruses. The sheet of cultured epithelial cells also permits the drainage of wound exudate without becoming saturated like a traditional wound dressing. Thus the need for frequent wound dressing changes in laser skin resurfacing wounds is reduced or even eliminated by the method of the invention.

Laser skin resurfacing procedures removes dermal tissue to various depths, depending on the skin feature which is treated. The methods disclosed herein are effective for promoting healing of laser skin resurfacing wounds of the epidermis and dermis because the sheet of cultured epithelial cells releases wound healing agents which, inter alia, promote proliferation and/or differentiation of the cell types which constitute the epidermis and dermis. Thus, healing of laser skin resurfacing wounds of the epidermis and dermis is enhanced using the present methods.

The methods of the invention can be applied to any patient who has undergone a laser skin resurfacing procedure. Although a majority of the laser skin resurfacing procedures are performed on the skin of the face, any other site of skin resurfacing is equally responsive to the methods disclosed herein.

A subject is treatable according to the methods disclosed herein regardless of the subject's genotype because the healing process promoted by the application of a sheet of cultured epithelial cells is not specific to the genetic makeup of the subject. Thus, the cells which constitute the sheet of cultured epithelial cells can be derived from multiple sources, e.g. from a mixed population of donors, or from any individual donor. Because the laser skin resurfacing procedure does not remove all cells capable of forming epidermis (stem cells), these cells will fill in the wound to create the resurfaced skin. Thus, the method accommodates application of non-syngeneic or non-autologous cells. In other words, the sheet of cells is not an autograft. The sheet of cultured epithelial cells is not required to be autologous because the cells of the sheet will not form the healed skin, but instead will promote the restoration of that skin from undamaged stem cells.

The method also contemplates the use of xenogeneic cells (i.e. from other species) in the sheet of cultured epithelial cells. Xenogencic cells optionally may be genetically manipulated to release a desired spectrum of wound healing agents such as human growth factors, cytokines and the like.

Preferably, the sheet of cultured epithelial cells substantially covers the laser resurfacing wound. The surface area which can be covered is not limited by the ability to grow sheets of sufficient size, but it is not intended to imply that only a single sheet of cells must be used to cover a wound site. Depending on the availability and handling properties of a sheet of sufficient size to entirely cover a wound, sheets of cells which each are insufficient to cover a wound may be combined to effect substantial coverage of a laser skin resurfacing wound.

The sheet of cultured epithelial cells can be composed of virtually any epithelial cells, and preferably is composed of those capable of forming a sheet (see, e.g., PCT Patent Application PCT/US95/14648). The sheets may be composed of multiple types of cells, e.g. keratinocytes and fibroblasts, or may be composed of a single type of cells. Preferably, the sheet of cultured epithelial cells consists essentially of epidermal keratinocytes. Green and collaborators described a method for culturing human epidermal keratinocytes (Rheinwald & Green, *Cell* 6:331–343, 1975), that has been extended to some other cultured epithelial cell types. Under such culture conditions, stratified epithelial sheets suitable for transplantation onto large burn surfaces, ulcerations and other skin wounds are obtained (Gallico et al., *New Eng. J Med.* 311:448–451, 1984; Heighten et al., *J Am. Acad. Dermatol.* 14:399–405, 1986). The cultured epithelia obtained through this procedure have also been used as allografts for temporary wound dressing for burns (T. J. Phillips et al., *J Am. Acad Dermatol.* 21:191, 1989; Bolivar-Flores et al., *Burns* 16:3–8, 1990). Cultured epithelial sheets prepared as described in the above-referenced articles arc useful in the methods of the present invention.

In certain embodiments of the invention, the sheet of cultured epithelial cells which is applied to the laser skin resurfacing wound is a preserved sheet of cultured epithelial cells. Preserved sheets of cultured epithelial cells and preferred methods for their preparation are disclosed in PCT Patent Application PCT/US95/14648. Other methods for preservation of cultured epithelial cell sheets are based on the use of glycerol or dimethyl sulfoxide as cryoprotectants, following a specific freezing protocol (see Cancedda and Dc Luca, 1994, U.S. Pat. No. 5,298,417). Still other preservation methods are based on cryopreservation using media containing both cell-penetrating glass-forming agents (specifically glycerol) and non-penetrating protectant agents (preferably polyvinylpyrrolidone (PVP), dextran or hydroxyethyl starch) (see Tubo et al, 1992, U.S. Pat. No. 5,145,770).

In one important embodiment, the sheet of cultured epithelial cells is preserved in a dried state, for example as described in PCT patent application PCT/US95/14648. In such a case, the preserved sheet can be directly applied to the wound without rehydration, or can be rehydrated and subsequently applied to the wound site. Rehydration can be achieved by placing the sheet in a solution having physiologically-acceptable parameters (such as pH and osmolarity) for a time sufficient to rehydrate the cultured epithelial cells. Of course, the rehydration process must maintain the structural and functional characteristics of the cultured epithelial sheet. Rehydration solutions include phosphate-buffered saline, Tris-buffered saline, Ringer's solution, and the like.

In other embodiments, the sheet of cultured epithelial cells can be preserved in a frozen state, for instance as described in PCT Patent Application PCT/US95/14648. When a frozen cultured epithelial cell sheet is used according to the invention, the sheet is thawed prior to applying it to the laser skin resurfacing wound. Methods for thawing the culture epithelial cell sheet which do not compromise the structural or functional integrity of the sheet can be used and will be known to one of ordinary skill in the art.

Optionally, the sheet of cultured epithelial cells can be applied to the laser skin resurfacing wound on a backing to facilitate manipulation of the sheet. Suitable backings include gauze, plastics, silicones, hydrogels and dextrans. When applied with a backing, the backing optionally can be removed after positioning the cell sheet at the wound site, and the cell sheet covered with a dressing. Alternatively, the backing can be left attached to the cell sheet to serve as an outer protectant layer. The cells may also be attached to (e.g., grown on) a substratum as disclosed in U.S. patent application Ser. No. 08/337,162, such as microbeads, hyaluronic acid, collagen, fibrin glue, synthetic products and the like. Preferably, synthetic products useful in the invention include polymers, particularly dermatologically-acceptable polymers as will be known to the skilled artisan. In such cases, the substratum can be attached to a backing if desired. The cultured epithelial cells can also be mixed with a gel, and then applied to the laser resurfacing wound.

EXAMPLE

This example describes the treatment of a subject having laser skin resurfacing wounds with the disclosed epithelial cell sheets and with the traditional method of healing such wounds. The subject is subjected to excimer laser treatment of periorbital rhytides.

Epithelial cell sheets are prepared as described in PCT Patent Application PCT/US95/14648. Briefly, epidermal sheets were obtained by culturing human neonatal foreskin keratinocytes, using the procedures developed by Rheinwald & Green (1975, supra). The epithelial sheets were detached from culture dishes using Dispase II (Boehringer Mannheim) at a final concentration of 2.5 mg/ml. After detaching from culture dishes, the epithelial sheets are washed with phosphate buffered saline (PBS) at room temperature, optionally are mounted in or on a backing material, such as Vaseline coated gauze, and are used as needed. If the epithelial cell sheets are to be preserved for late use, then following the PBS wash the sheets are incubated for 10 minutes with preservation solution consisting in Dulbecco-Vögt modification of Minimal Esential Medium (DMEM) containing glucose and human serum albumin; if desired, preservation solution may be buffered with 20.0 mM HEPES. After incubation, the preservation solution is aspirated leaving the minimum volume of solution in the vessel containing the epithelium. Afterwards, epithelia, which may be mounted on a backing material, are kept in heat-sealed bags and frozen as described in PCT/US95/14648. If used after freezing, epithelial sheets are thawed in culture medium (Dulbecco-Vögt modification to Minimum Essential Medium, DMEM). Alternatively, the epithelial sheets can be dried.

An epithelial sheet is removed from the container in which it is stored, and applied aseptically to the laser skin resurfacing wound present on the right periorbital region of the subject. The epithelial sheet is covered with a gauze dressing. The left periorbital region of the subject is treated according to standard laser resurfacing wound healing practices. The subject observes reduced pain and discomfort during the healing process at the site of the right periorbital laser resurfacing wound, which is treated with the epithelial cell sheet, relative to left laser skin resurfacing wound, which is treated with the art standard ointments and dressings. The epithelial cell sheet is removed before the treatment with the standard dressing with ointment can be discontinued, indicating that the epithelial cell sheet shortens the time required for complete healing of the laser skin resurfacing wounds. Re-epithelialization typically occurs within 4-6 days.

All patents and other documents disclosed in this application are incorporated in their entirety herein by reference.

While the invention has been described with respect to certain embodiments, it should be appreciated that many modifications and changes may be made by those of ordinary skill in the art without departing from the spirit of the invention. It is intended that such modification, changes and equivalents fall within the scope of the following claims.

What is claimed is:

1. A method for promoting healing of a laser skin resurfacing wound comprising applying to the laser skin resurfacing wound of a subject in need of such treatment a preserved sheet of allogeneic or xenogeneic cultured epithelial cells that substantially covers the wound, the sheet of cultured epithelial cells comprising cultured epidermal keratinocytes, wherein the sheet of cultured epithelial cells is applied to the wound on a backing layer.

2. The method of claim 1, wherein the preserved sheet of cultured epithelial cells is dried.

3. The method of claim 1, wherein the preserved sheet of cultured epithelial cells is frozen and wherein the method further comprises thawing the preserved sheet of culture cells prior to applying to the laser skin resurfacing wound.

4. The method of claim 1, wherein the backing layer is a gauze mesh.

5. The method of claim 1, further comprising covering the sheet of cultured epithelial cells, after application to the wound, with a dressing.

6. The method of claim 1, wherein the cultured epithelial cells are attached to a substratum or mixed with a gel.

7. The method of claim 6, wherein the substratum is selected from the group consisting of microbeads, hyaluronic acid, collagen, fibrin glue and polymers.

* * * * *